United States Patent
Woodbine et al.

(10) Patent No.: US 12,042,598 B2
(45) Date of Patent: Jul. 23, 2024

(54) SYSTEM AND METHOD FOR DOSING VAPORIZER JOURNALING DEVICE

(71) Applicant: GoFire, Inc., Wheat Ridge, CO (US)

(72) Inventors: John Jesse Woodbine, Lafayette, CO (US); Max J Schnurrenberger, Denver, CO (US); Peter William Calfee, Dorset, VT (US)

(*) Notice: Subject to any disclaimer, the term of this patent is extended or adjusted under 35 U.S.C. 154(b) by 500 days.

(21) Appl. No.: 17/320,026

(22) Filed: May 13, 2021

(65) Prior Publication Data
US 2021/0361885 A1    Nov. 25, 2021

Related U.S. Application Data

(60) Provisional application No. 63/029,260, filed on May 22, 2020.

(51) Int. Cl.
*A61M 11/04* (2006.01)
*A61M 11/00* (2006.01)
*G06F 1/28* (2006.01)

(52) U.S. Cl.
CPC ......... *A61M 11/042* (2014.02); *A61M 11/005* (2013.01); *G06F 1/28* (2013.01); *A61M 2205/3327* (2013.01); *A61M 2205/3553* (2013.01); *A61M 2205/3584* (2013.01); *A61M 2205/52* (2013.01); *A61M 2205/8206* (2013.01)

(58) Field of Classification Search
None
See application file for complete search history.

(56) References Cited

U.S. PATENT DOCUMENTS

| 4,934,358 A | 6/1990 | Nilsson et al. |
|---|---|---|
| 4,947,875 A | 8/1990 | Brooks et al. |

(Continued)

FOREIGN PATENT DOCUMENTS

| EP | 2207528 | 10/2013 |
|---|---|---|
| EP | 3099363 | 12/2016 |

(Continued)

OTHER PUBLICATIONS

PCT International Search Report for International Application PCT/US2021/031333, search report data of mailing 41 Aug. 2021 (Aug. 31, 2021).

*Primary Examiner* — Hua Lu
(74) *Attorney, Agent, or Firm* — Daniel W. Roberts; Law Offices of Daniel W. Roberts, LLC (57) ABSTRACT

Provided is a system and method for a vaporizer journaling device. The journaling adapter has a housing providing a first coupler at a first end for engaging a hand-held vaporizer device and a second coupler at a second end for engaging a removable power supply. The housing encloses a first electrical pathway structured and arranged to interconnect an engaged vaporizer device and the removable power supply. A wireless transceiver is also enclosed and structured and arranged for wireless communication with at least one remote computing device. A control system having at least one processor is structured and arranged to sense a flow of current through the first electrical pathway to the vaporizer device, detect a vaporizing event, and communicate by the wireless transceiver each vaporizing event to the at least one remote computing device. An associated method of use is also provided.

33 Claims, 5 Drawing Sheets

(56) References Cited

U.S. PATENT DOCUMENTS

| | | | |
|---|---|---|---|
| 5,284,133 A | 2/1994 | Burns et al. | |
| 6,772,756 B2 | 8/2004 | Shayan | |
| 6,814,083 B2 | 11/2004 | Likness et al. | |
| 6,830,046 B2 | 12/2004 | Blakley | |
| 7,088,914 B2 | 8/2006 | Whittle et al. | |
| 7,164,993 B2 | 1/2007 | Likness et al. | |
| 7,540,286 B2 | 6/2009 | Cross et al. | |
| 7,905,230 B2 | 3/2011 | Schuler | |
| 8,464,706 B2 | 6/2013 | Crockford et al. | |
| 8,550,069 B2 | 10/2013 | Alelov | |
| 8,602,037 B2 | 12/2013 | Inagaki | |
| 8,851,068 B2 | 10/2014 | Cohen et al. | |
| 8,897,628 B2 | 11/2014 | Conley et al. | |
| 8,899,239 B2 | 12/2014 | Hon | |
| 8,910,630 B2 | 12/2014 | Todd | |
| 9,220,294 B2 | 12/2015 | McCullough | |
| 9,320,301 B2* | 4/2016 | Memari | H02J 7/0044 |
| 9,380,813 B2 | 7/2016 | McCullough | |
| 9,462,832 B2 | 10/2016 | Lord | |
| 10,806,179 B2* | 10/2020 | Bajpai | A24F 40/46 |
| 2005/0277912 A1 | 12/2005 | John | |
| 2006/0092071 A1 | 5/2006 | Andermo | |
| 2006/0289005 A1 | 12/2006 | Jones | |
| 2010/0250280 A1 | 9/2010 | Sutherland | |
| 2011/0118694 A1 | 5/2011 | Yodfat | |
| 2012/0029442 A1 | 2/2012 | Boyd | |
| 2013/0152922 A1* | 6/2013 | Benassayag | A61M 11/042 |
| | | | 128/202.21 |
| 2013/0220315 A1 | 8/2013 | Conley | |
| 2013/0245545 A1 | 9/2013 | Arnold | |
| 2013/0245604 A1 | 9/2013 | Kouyoumjian | |
| 2013/0340775 A1* | 12/2013 | Juster | H04L 12/1827 |
| | | | 131/273 |
| 2014/0000638 A1 | 1/2014 | Sebastian | |
| 2014/0116455 A1 | 5/2014 | Youn | |
| 2014/0202477 A1 | 7/2014 | Qi et al. | |
| 2014/0243749 A1 | 8/2014 | Edwards et al. | |
| 2014/0278250 A1 | 9/2014 | Smith et al. | |
| 2014/0322782 A1 | 10/2014 | Baym | |
| 2014/0345633 A1 | 11/2014 | Talon et al. | |
| 2014/0345635 A1 | 11/2014 | Rabinowitz et al. | |
| 2015/0039591 A1 | 2/2015 | Ding et al. | |
| 2015/0053217 A1* | 2/2015 | Steingraber | A24F 40/50 |
| | | | 131/329 |
| 2015/0136158 A1 | 5/2015 | Stevens et al. | |
| 2015/0142387 A1 | 5/2015 | Alarcon et al. | |
| 2015/0181945 A1 | 7/2015 | Tremblay | |
| 2015/0245660 A1 | 9/2015 | Lord | |
| 2015/0272220 A1 | 10/2015 | Spinka et al. | |
| 2015/0297859 A1 | 10/2015 | Spandorfer | |
| 2015/0320948 A1 | 11/2015 | Eicher | |
| 2015/0327596 A1 | 11/2015 | Alarcon et al. | |
| 2015/0332379 A1 | 11/2015 | Alarcon | |
| 2015/0366266 A1 | 12/2015 | Shabat | |
| 2016/0007651 A1 | 1/2016 | Ampolini et al. | |
| 2016/0021930 A1 | 1/2016 | Minskoff et al. | |
| 2016/0089508 A1 | 3/2016 | Smith et al. | |
| 2016/0106935 A1 | 4/2016 | Sezan | |
| 2016/0106936 A1 | 4/2016 | Kimmel | |
| 2016/0143361 A1 | 5/2016 | Juster et al. | |
| 2016/0157524 A1* | 6/2016 | Bowen | A61M 15/06 |
| 2016/0200463 A1 | 7/2016 | Hodges | |
| 2016/0211693 A1* | 7/2016 | Stevens | H04W 48/16 |
| 2016/0219932 A1 | 8/2016 | Glaser | |
| 2016/0219933 A1 | 8/2016 | Henry, Jr. et al. | |
| 2016/0219938 A1* | 8/2016 | Mamoun | G05B 15/02 |
| 2016/0278435 A1 | 9/2016 | Choukroun et al. | |
| 2016/0309784 A1 | 10/2016 | Silvestrini et al. | |
| 2016/0309788 A1* | 10/2016 | Hawes | A61M 15/06 |
| 2016/0309789 A1 | 10/2016 | Thomas, Jr. | |
| 2016/0325058 A1 | 11/2016 | Samson | |
| 2016/0331027 A1 | 11/2016 | Cameron | |
| 2016/0331913 A1 | 11/2016 | Bourque | |
| 2016/0337141 A1 | 11/2016 | Cameron | |
| 2016/0356751 A1 | 12/2016 | Blackley | |
| 2016/0360790 A1* | 12/2016 | Calfee | A24F 40/46 |
| 2016/0363570 A1 | 12/2016 | Blackley | |
| 2016/0363917 A1 | 12/2016 | Blackley | |
| 2016/0370335 A1 | 12/2016 | Blackley | |
| 2017/0014582 A1 | 1/2017 | Skoda | |
| 2017/0273357 A1* | 9/2017 | Barbuck | H05B 3/04 |
| 2018/0043115 A1* | 2/2018 | Gould | A61M 11/042 |
| 2018/0177958 A1 | 2/2018 | Wilder | |
| 2018/0116281 A1* | 5/2018 | Anderson, Jr. | A61M 15/0065 |
| 2018/0177231 A1* | 6/2018 | Woodbine | A24F 40/65 |
| 2018/0043114 A1 | 8/2018 | Shears | |
| 2018/0263283 A1 | 9/2018 | Popplewell | |
| 2018/0263288 A1* | 9/2018 | Goldstein | A61M 11/042 |
| 2018/0266685 A1* | 9/2018 | Fisten | F23Q 7/16 |
| 2018/0353682 A1 | 12/2018 | Laurence | |
| 2019/0022345 A1* | 1/2019 | Kotch | A61M 16/145 |
| 2019/0058970 A1 | 2/2019 | Baker et al. | |
| 2019/0111220 A1 | 4/2019 | Richardson | |
| 2019/0325287 A1 | 10/2019 | Strange | |
| 2020/0237004 A1* | 7/2020 | Larsen | A24F 40/20 |
| 2020/0352249 A1* | 11/2020 | Achtien | A61M 15/0066 |
| 2021/0251285 A1* | 8/2021 | Pasternack | A24F 40/50 |
| 2022/0271466 A1* | 8/2022 | Kirsh | A24F 40/50 |
| 2023/0093650 A1* | 3/2023 | Pasternack | A24F 40/50 |
| | | | 131/273 |

FOREIGN PATENT DOCUMENTS

| | | |
|---|---|---|
| EP | 3102266 | 12/2016 |
| GB | 2524779 | 10/2015 |
| WO | WO03097141 | 11/2003 |
| WO | WO2016050247 | 4/2016 |
| WO | WO2016064906 | 4/2016 |
| WO | WO2016172802 | 11/2016 |
| WO | WO 2016-187110 | 12/2016 |
| WO | WO2016187695 | 12/2016 |

* cited by examiner

SYSTEM AND METHOD FOR DOSING VAPORIZER JOURNALING DEVICE

CROSS REFERENCE TO RELATED APPLICATIONS

This application claims the benefit under 35 U.S.C. § 119(e) of U.S. Provisional Application No. 63/029,260 filed May 22, 2020 and entitled SYSTEM AND METHOD FOR DOSING VAPORIZER JOURNALING ADAPTER, the disclosure of which is incorporated herein by reference.

In addition, the following patent applications and patents are incorporated by reference herein in their entireties: U.S. patent application Ser. No. 17/190,044 entitled SYSTEM AND METHOD FOR METERED DOSING VAPORIZER (hereinafter "'044 app"), U.S. patent application Ser. No. 15/391,829 entitled SYSTEM AND METHOD FOR MANAGING CONCENTRATE USAGE OF A USER (hereinafter "'829 app"), U.S. patent application Ser. No. 16/592,674 entitled SYSTEM AND METHOD FOR MANAGING CONCENTRATE USAGE OF A USER (hereinafter "'674 app"), U.S. Patent Application Ser. No. 62/660,974 entitled SMART VAPORIZER AND SYSTEM FOR CONCENTRATE PRODUCTS (hereinafter "'974 app"), U.S. Patent Application Ser. No. 62/721,699 entitled VAPORIZER CARTRIDGE SYSTEM AND METHOD OF USE (hereinafter "'699 app"), U.S. patent application Ser. No. 16/541,062 entitled SYSTEM AND METHOD FOR VAPORIZING CARTRIDGE SYSTEM WITH DIFFUSER (hereinafter "'062 app"), U.S. patent application Ser. No. 16/559,556 entitled SYSTEM AND METHOD FOR DETERMINING AN APPROPRIATE DOSE OF A PRODUCT (hereinafter "'556 app"), and U.S. Pat. No. 10,888,665 entitled SYSTEM AND METHOD FOR MULTI-MODAL DOSING DEVICE (hereinafter "'665 patent"), U.S. Pat. No. 10,888,666 entitled SYSTEM AND METHOD FOR MULTI-MODAL DOSING DEVICE (hereinafter "'666 patent"), and U.S. Pat. No. 10,834,967 entitled SYSTEM AND METHOD FOR MANAGING CONCENTRATE USAGE OF A USER (hereinafter "'967 patent").

FIELD OF THE INVENTION

The present invention relates generally to a journaling adapter structured and arranged so as to attach to a power source and a hand-held vaporizing device, which may optionally and advantageously contain a vaporizing cartridge of vaporizable concentrate. The product within the cartridge is generally understood to be a liquid or oil concentrate. In particular, the present invention presents a system for the precise tracking of use of the attached cartridge and communication of that usage to at least one user.

BACKGROUND

Often referred to as e-cigarettes, hand-held vaporizers, "vapes" or the like, the general device is understood and appreciated to be a hand-held electronic device that provides a user with a vapor for medical or recreational inhalation In general, these devices are generally understood to comprise an electrically activated vaporizer, within a housing that provides a mouthpiece and typically encloses a cartridge or reservoir of the material to be vaporized.

For some models the battery powering the vaporizer may be removable, while in others it is permanent. Of course, the batteries may be rechargeable as well.

With a traditional smoking device where fire is used to combust a material into smoke, as with a pipe, cigarette or cigar, the inhalation by the user draws air through the burning medium which furthers the burning action, and creates the draw of smoke.

With vaporizer devices, although the draw of air by the user may be used to trigger device operation, the transition of the inhaled substance from an initial state to a vapor state is not accomplished by fire. Most commonly, the material to be vaporized is provided in a liquid form—such as an oil-based liquid, that serves as a transport medium to initially store the inhalant compound, and later convey the inhalant compound into a vaporizer element such that the liquid is transformed into a vapor. This vaporized form of the compound is inhaled by the user.

With the increasing proliferation of plant based medicinal products, proper dosage is an important part of patient care for consistent and reliable treatment of a given condition or ailment. Indeed, in some cases different dosages of the same product may be appropriate for different conditions or ailments—thus further emphasizing the importance of proper product dosing for a specific condition or ailment.

In addition, vapes have grown in application for smoking cessation programs regarding traditional tobacco products with the realization that reducing the quantity and frequency of nicotine delivery can be more effective than a "cold turkey" stopping effort. But here again, helping the user maintain control and knowledge of his or her progress is often an important component of their cessation effort.

With the increasing proliferation of e-cigarettes, handheld vaporizers or the like, tracking usage is of vital importance for many users. When combined with a dosing vaporizer the value is amplified considerably. Especially in a medical environment, or as part of a cessation program usage tracking is of considerable value.

Hence there is a need for a method and system that is capable of overcoming one or more of the above identified challenges.

SUMMARY OF THE INVENTION

Our invention solves the problems of the prior art by providing a novel journaling adapter to be used with a vaporizing cartridge and a power source, to communicate usage information to a remote computing device. The powered journaling adapter communicating to a central server allows a third party to monitor and ensure compliance with a cessation program, or for the user, or a $2^{nd}$ user to monitor and track usage of the vaporizing cartridge.

In particular, and by way of example only, according to at least one embodiment, provided is a vaporizer journaling device including: a housing providing a first coupler at a first end for engaging a hand-held vaporizer device and a second coupler at a second end for engaging a removable power supply; the housing substantially enclosing: a first electrical pathway within the housing, the first electrical pathway structured and arranged to interconnect the engaged vaporizer device and the removable power supply; a wireless transceiver structured and arranged for wireless communication with at least one remote computing device; a control system having at least one processor, the control system structured and arranged to: sense a flow of current through the first electrical pathway to the vaporizer device; detect a vaporizing event; and communicate by the wireless transceiver each vaporizing event to the at least one remote computing device.

In yet another embodiment, provided is a vaporizer journaling device including: a housing providing a first coupler at a first end for engaging a hand-held vaporizer device and a second coupler at a second end for engaging a removable power supply; the housing substantially enclosing: a first electrical pathway within the housing, the first electrical pathway structured and arranged to interconnect the engaged vaporizer device and the removable power supply; a switch disposed along the first electrical pathway and operable to interrupt the pathway; at least one sensor structured and arranged to detect at least one event; a processor; a non-volatile memory coupled to the processor having executable instructions to direct the operation of the processor to control the switch and the at least one sensor for the detection of one or more events; a wireless transceiver coupled to the processor and the non-volatile memory and operable to communicate with at least one remote computing device; and wherein in response to the detection of one or more events by the at least one sensor, the processor generating data communicated by the wireless transceiver to the at least one remote computing system.

For yet another embodiment, provided is a method for using a vaporizer journaling device, including: providing a journaling device comprising: a housing providing a first coupler at a first end for engaging a hand-held vaporizer device and a second coupler at a second end for engaging a removable power supply; the housing substantially enclosing: a first electrical pathway within the housing, the first electrical pathway structured and arranged to interconnect the engaged vaporizer device and the removable power supply; a switch disposed along the first electrical pathway and operable to interrupt the pathway; at least one sensor structured and arranged to detect at least one event; a processor; a non-volatile memory coupled to the processor having executable instructions to direct the operation of the processor to control the switch and the at least one sensor for the detection of one or more events; a wireless transceiver coupled to the processor and the non-volatile memory and operable to communication with at least one remote computing device; and wherein in response to the detection of one or more events by the at least one sensor, the processor generating data communicated by the wireless transceiver to the at least one remote computing system; disposing the journaling device between a vaporizer device and a removable power supply; sensing a flow of current through the first electrical pathway to detect a vaporizing event; and reporting at least the vaporizing event to the at least one remote computing device.

DETAILED DESCRIPTION

Before proceeding with the detailed description, it is to be appreciated that the present teaching is by way of example only, not by limitation. The concepts herein are not limited to use or application with a specific dosing vaporizer system. Thus, although the instrumentalities described herein are for the convenience of explanation shown and described with respect to exemplary embodiments, it will be understood and appreciated that the principles herein may be applied equally in other types of systems involving dosing vaporizer systems.

This invention is described with respect to preferred embodiments in the following description with reference to the Figures, in which like numbers represent the same or similar elements. Further, with respect to the numbering of the same or similar elements, it will be appreciated that the leading values identify the Figure in which the element is first identified and described, e.g., element 100 first appears in FIG. 1.

Various embodiments presented herein are descriptive of apparatus, systems, articles of manufacturer, or the like for systems and methods involving providing a certificate by way of a browser extension. In some embodiments, an interface, application browser, window or the like may be provided that allows the user of the computing device to direct behavior of the computing device.

Moreover, some portions of the detailed description that follows are presented in terms of the manipulation and processing of data bits within a computer memory. The steps involved with such manipulation are those requiring the manipulation of physical quantities. Generally, though not necessarily, these quantities take the form of electrical or magnetic signals capable of being stored, transferred, combined, compared and otherwise manipulated. Those skilled in the art will appreciate that these signals are commonly referred to as bits, values, element numbers or other clearly identifiable components.

It is of course understood and appreciated that all of these terms are associated with appropriate physical quantities and are merely convenient labels applied to these physical quantifies. Moreover, it is appreciated that throughout the following description, the use of terms such as "processing" or "evaluating" or "receiving" or "outputting" or the like, refer to the action and processor of a computer system or similar electronic computing device that manipulates and transforms data represented as physical (electrical) quantities within the computer system's memories into other data similarly represented as physical quantities within the computer system's memories.

The present invention also relates to apparatus for performing the operations herein described. This apparatus may be specifically constructed for the required purposes as are further described below, or the apparatus may be a general-purpose computer selectively adapted or reconfigured by one or more computer programs stored in the computer upon computer readable storage medium suitable for storing electronic instructions.

To further assist in the following description, the following defined terms are provided.

"User"—typically a person or at the very least a computing device used by a person who is known to the dosing system, or an administration system that is in communication with the dosing system in the sense that the he or she has established a User account by providing a threshold of data, e.g. attributes, to identify themselves. Typically, it is expected that the Users' interactions with the dosing system or the related administration system will also serve to establish additional Attributes about themselves.

"Remote First Computing Device"—the portable computing device having at least one processor that is used by the person/User desiring a dosage of a Product.

"Dosing System"—The system to which Users connect when requesting a dose/dosage of a Product. The Dosing System maintains or at least interacts with a Database of Products.

"Database of Products"—an indexed set of records correlating Products, one or more Constituents for each product, Established Reasons for which Products have been used, dosages associated to Reasons, and User evaluation feedback. The Database of Products may be established as a relational database and may be localized upon one or more computing systems in a specific location, or distributed such as in a cloud computing space.

"Product"—a compound that may be provided as a liquid, liquid concentrate, edible medium, inhalant, tablet, semi-solid, cream, or other form that may be consumed by a physical person. Generally, this is understood and appreciated to be a plant based medicinal compound. However, it is understood and appreciated that in varying embodiments, a Product or Products may also be a pharmaceutical, organic, and/or synthetically derived compound. Further still, for yet another embodiment, a Product may be provided as a combination of elements selected from the group consisting of, plant, animal, mineral, organic, pharmaceutical, and synthetic compounds.

"Attribute"—an element of data that is distinct to the Product, such as a bar code, QR code, listing of actual constituents and levels, or other data, the Attribute permitting specific identification of one or more constituent and apparent level of the one or more consistent for a specific product.

With respect to the above defined terms, it is understood and appreciated that for at least one embodiment, each module or system is implemented as a collection of independent electronic circuits packaged as a unit upon a printed circuit board or as a chip attached to a circuit board or other element of a computer so as to provide a basic function within a computer. In varying embodiments, one or more modules may also be implemented as software that adapts a computer to perform a specific task or basic function as part of a greater whole. Further still, in yet other embodiments one or more modules may be provided by a mix of both software and independent electronic circuits.

To briefly summarize, the present invention pertains to embodiments for a system and method for a vaporizer journaling device. The journaling device is user installed between the vaporizer and its power source, such as a battery. The journaling device is structured and arranged to at the very least monitor, and additionally control, the use of the vaporizing device to assist the user in complying with regimented or structured use of the vaporizer, such as for a smoking cessation program, the treatment of one or more ailments, and/or recreational purposes.

This summary may be more fully appreciated with respect to the following description and accompanying figures.

Figure 1:
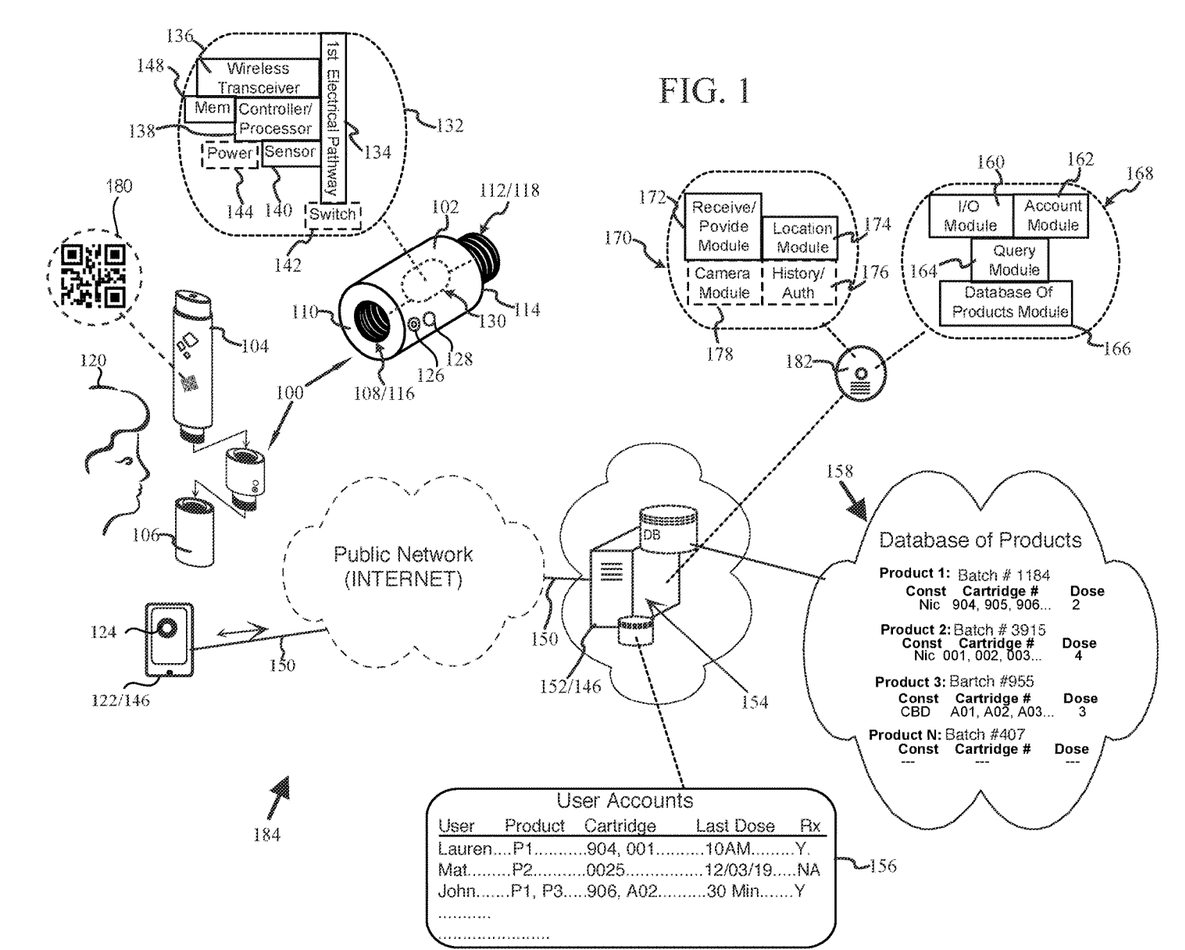
FIG. 1 illustrates an overview of an embodiment for a journaling device and a system incorporating a journaling device in accordance with at least one embodiment of the present invention.

Turning now to the drawings, and more specifically, FIG. 1, there is shown a high-level diagram of an embodiment of a journaling adapter, also herein referred to as a journaling device 100, hereinafter "JD 100". For at least one embodiment, the JD 100 is provided as a simple unitary device, the primary housing 102 of which is generally barrel like in appearance. For ease of use and ergonomic simplicity, the diameter or cross section geometry of the housing 102 may be selected to be substantially the same as the hand-held vaporizer device 104 to which the JD 100 is to be connected.

Moreover, JD 100 is structured and arranged to be disposed between the vaporizer device 104 and its intended power supply 106, which is typically a battery. More specifically, the JD 100 provides a first coupler 108 at a first end 110 for coupling with a removable power supply 106 and a second coupler 112 at a second end 114 for coupling with the hand-held vaporizer device 104.

As noted above, the vaporizer device 104 is structured and arranged to transform a product stored within a reservoir, such as a cartridge, into an inhalable vapor by means of heat (to vaporize), vibration (to nebulize) or such other process as is selected to transform a quantity of product into an inhalable vapor. As used herein, the term "vaporizing device" is understood and appreciated to apply to any and all such devices regardless of the nature of the system employed for the transformation of the product to a vapor.

Key for this transformation of Product to vapor is the use of electrical energy to impart heat (to vaporize) or vibration (to nebulize) a dispensed quantity of the Product material so as to transition it from a liquid to a vapor. More specifically, by the application of heat, vibration, or other process to transform the liquid Product to an inhalable vapor, these processes are understood and appreciated to require electrical energy. This usage of electrical energy as drawn from the power supply 106, is sensed by the JD 100, and thereby used to determine a vaporizing event.

For at least one embodiment, the hand-held vaporizer device 104 is an embodiment of a vaporizer as set forth and disclosed in the '044 app entitled SYSTEM AND METHOD FOR METERED DOSING VAPORIZER, as noted above and incorporated herein by reference.

For at least one embodiment, the first coupler 108 is a first set of threads 116 and the second coupler is a second set of threads 118. Further still, for at least one embodiment either or both of the first coupler 108 and the second coupler 112 are provided as a swivel coupling—permitting the coupling to be rotated without requiring rotation of the JD 100, the vaporizer device 104 or the power supply 106.

It will also be appreciated that the power supply 106 is a portable battery. More specifically, for at least one embodiment the power supply 106 is understood and appreciated to be a 510-battery. The 510-battery is so named for the threaded connector and the number of threads provided by the connector to make a threaded connection with a mating connector.

As 510-batteries have become essentially the present standard for removable power supplies 106 for many vaporizing devices 104, it will be understood and appreciated that for at least one embodiment the first set of threads 116 are female 510-connector threads and the second set of threads 118 are male 510-connector threads. As such, an embodiment of JD 100 structured and arranged for 510-battery connection may be easily disposed between the vaporizer device 104 and the 510-battery provided as the power supply 106. Of course, it will be understood and appreciated that alternative embodiments of JD 100 may be provided for use with a power supply 106 other than a 510-battery without departure from the teachings herein.

As is shown in FIG. 1, a User 120 of vaporizer device 104 having JD 100 attached is shown having a Remote First Computing Device 122. For at least one embodiment, it will be understood and appreciated that JD 100 provides few if any external user operable buttons, for as is further set forth below, in accordance with at least one embodiment, the JD 100 is intended for use with a remote application 124 that has been provided to a Remote First Computing Device 122 of User 120, such as an iPhone®, Android® or other similar device. Moreover, it will be understood and appreciated that the Remote First Computing Device 122 has at least a processor such as a CPU, memory and a wireless transceiver which are adapted by hardware and/or software to perform various computing functions, including the exchange of data with other computing devices.

For at least one embodiment, the JD 100 may provide at least one indicator light 126 and or a reset button 128, but it will be understood and appreciated that embodiments of the JD 100 may be provided without such elements—a window for reset/configuration being initiated upon the connection of the JD 100 to power supply 106, such as a 510-battery. Of course, it will also be understood and appreciated that if a reset/configuration is not initiated by the user upon connection to a power source, for at least one embodiment, the JD 100 will continue operating in accordance with the last established configuration.

The ability of JD 100 to monitor, if not control the vaporizer device 104 is achieved at least in part by an internal control system 130. For at least one embodiment, the internal control system 130 is provided at least in part with the elements/components as shown in the bubble callout 132. For at least one embodiment, within the housing 102, JD 100 provides a first electrical pathway 134 structured and arranged to interconnect the vaporizer device 104 with the power supply 106 when the JD 100 is disposed therebetween. In addition, the housing 102 encloses a wireless transceiver 136, a controller 138, at least one sensor 140, and optionally a switch 142 and/or internal power source 144.

The controller 138 is understood and appreciated to be a computer processor such as a CPU. Non-volatile memory 148 is coupled to the controller 138, and provided executable instructions to direct the operation of the controller 138 and the at least one sensor 140 for the detection of a vaporizing event. The wireless transceiver 136 is also coupled to the controller 138 and is structured and arranged for wireless communication with at least one remote computing device 146.

For at least one embodiment the wireless transceiver 136 operates in the form of Bluetooth Low Energy (BLE). For at least one alternative embodiment the wireless transceiver 136 operates in the form of near field communication (NFC). For yet another embodiment the wireless transceiver 136 operates in the form of cellular communication (LTE, 4G, 3G). For at least one embodiment, the wireless transceiver 136 is a wireless network component.

Moreover, the wireless transceiver 136 is understood and appreciated to permit the wireless transfer of data as between the JD 100 and the at least one remote computing device 146. Further still, for at least one embodiment the wireless transceiver 136 is structured and arranged to use existing wireless data technologies such that a JD 100 may be quickly and advantageously deployed in a new or existing environment without substantial burden to the user or caregiver assisting the user.

With respect to the above description, at least one embodiment of JD 100 may be summarized as including: a housing 102 providing a first coupler 108 at a first end 110 for engaging a hand-held vaporizer device 104 and a second coupler 112 at a second end 114 for engaging a removable power supply 108; the housing 102 substantially enclosing; a first electrical pathway 134 structured and arranged to interconnect the engaged vaporizer device 104 and the removable power supply 108; a wireless transceiver 136 structured and arranged for wireless communication with at least one remote computing device 146; a control system 130 having at least one processor, the control system 130 structured and arranged to: sense a flow of current through the first electrical pathway 134 to the vaporizer device 104; detect a vaporizing event; and communicate by the wireless transceiver 136 each vaporizing event to the at least one remote computing device 146.

As at least one advantage of the JD 100, is the advantageous ability to enhance use and/or compliance of the vaporizer device 104, before proceeding with a detailed review of the components for one or more embodiments of a JD 100, an overview of at least one system in which the JD 100 may be utilized may further assist in the understanding and appreciation of the advantages provided by embodiments of JD 100.

With respect to the greater context presented by FIG. 1, a user 120 is shown having a Remote First Computing Device 122 having an application ("App") 124 that adapts the Remote First Computing Device 122 for interaction with the JD 100 as disposed between the vaporizer device 104 and the power supply 106. As shown, the Remote First Computing Device 122 is in wireless communication 150 with the JD 100. For at least one embodiment, the Remote First Computing Device 122 is also enabled for wireless/network communications 150.

By such wireless communication 150 the Remote First Computing Device 122 may establish communication with at least one remote server system 152—e.g., a computing system that is distinct from the Remote First Computing Device 122 of the user 120. For at least one embodiment, the at least one remote server system 152 is a Dosing System 154. Further still, for at least one embodiment the Dosing System 154 is essentially the Dosing System as set forth and described in the '556 app entitled SYSTEM AND METHOD FOR DETERMINING AN APPROPRIATE DOSE OF A PRODUCT, as noted above and incorporated herein by reference, or an adapted variation thereof.

Moreover, the at least one remote server system 152 has user account records 156. In addition, for at least one embodiment, the at least one remote server system 152 also has a database of products 158. In varying embodiments, the user account records 156 and database of products 158 may be integrated as one database, or segregated as separate and distinct databases. For the embodiment, shown, the user records 156 are a component integrated with the at least one remote server system 152, aka Dosing System 154.

It will also be understood and appreciated that both Remote First Computing Device 122 and the at least one remote server system 152 are remote computing devices 146 to which the JD 100 communicates by way of the wireless transceiver 136. In general, the JD 100 will communicate indirectly with at least one remote server system 152 by way of the Remote First Computing Device 122 of the User 120. However, it will be understood and appreciated that for at least one alternative embodiment, the JD 100 may communicate directly through a network communication link (e.g. wireless communication 150) to the at least one remote server system 152, aka Dosing System 154.

For at least one embodiment, to permit JD 100 to advantageous monitoring and/or control the use of the vaporizer device 104, as indicated above the Remote First Computing Device 122 is provided with an App 124 which interfaces with the Dosing System 154.

Indeed, for at least one embodiment, the Dosing System 154 is provided by hardware and/or software adapting the physical remote server system 152 to provide at least an I/O module 160, an account module 162, a query module 164, and a database of products module 166. Moreover, for at least one embodiment, and with respect to FIG. 1, the JD 100 is implemented in a client & server type of computer system. More specifically, the server component 168 is provided by the I/O module 160, the account module 162 and the database of products module 166 as provided to the remote server system 152. The client component 170, aka App 124, is provided by the receive/provide module 172, an optional location module 174, an optional history/authorization module 176, and/or and the optional camera module 178.

With respect to the client, e.g. App 124, the receive/provide module 172 is structured and arranged to permit a user to receive and provide data to Dosing System 154 at a general level—to set up a user account and subsequently log in and to select among a variety of options such as a review of the User's history of use, to indicate the intention to initiate a new vaporization session, to record a completed vaporizing session, to request authorization for a vaporizing session, to provide identification of the Product intended for vaporizing use, etc. . . . . The receive/provide module 172 is effectively an I/O module, but it has been identified by a different label herein so as to avoid possible confusion with the I/O module of the Dosing System 154/Server component 168.

The optional location module 112 is typically a background application utilizing the location determining abilities of the Remote First Computing Device 122 to note the location of the User. The determination of location may be utilized in determining whether or not the User 120 is in a location permitting use of the vaporizer device 104.

The optional history/authorization module 176 may permit the App 124, and by incorporation thereupon the Remote First Computing Device 122, to operate in stand-alone/local mode—i.e., without interfacing with a Dosing System 154. Moreover, the receive/provide module 172 may permit the user 120 to establish a local account upon their Remote First Computing Device 122, with the history/authorization module 176 then engaging to determine if the User 120 can initiate a vaporization event with the vaporization device 104. This determination of authorization may be based on any number of factors—the last time a vaporization event was initiated, the duration of the last vaporization event, the location of the vaporization event, the nature of the Product, etc. . . . . In addition, the history/authorization module 176 may also be pre-programed with control parameters such as for how long the vaporization event should occur to achieve a proper transformation of Product to vapor.

As is further discussed below, for at least one embodiment the JD 100 is structured and arranged to identify the Product within the vaporizer device 104. This may be accomplished through a variety of options, such as but not limited to a transmitted signal, provided wirelessly or along one or more of the electrical connections established when the JD 100 is coupled to the vaporizer device 104; the detection of an RFID chip or tag; or other implemented methodology to permit an identification tag 180, and in some embodiments a unique identification tag 180, to be provided upon the vaporizer device 104 or its reservoir to identify the Product.

For some embodiments, the identification information 180 may be provided as a barcode, QR code, numeric code, alphanumeric, pictograph, or other visual data encoding element that may photographed by the camera of the Remote First Computing Device 122—the photograph being interpreted to extract the identification tag 180 which in turn may be provided to the JD 100 and/or the Dosing System 154.

For this potential use, the camera module 178 permits the User 120 to use the camera of the Remote First Computing Device 122 to acquire an Attribute, e.g., the identification tag 180, from the vaporizer device 104 or the Product contained therein. More specifically, the camera module 178 permits the User 120 to scan a bar code, UPC code, QR code, or other readable code or data so that the identity of the Product to be vaporized may be determined.

With respect to FIG. 1, the elements of the client component 170, aka App 124, and the server component 168, aka Dosing System 154 may be provided upon a non-transitory computer readable media, such as an optional disc 182, a USB drive (not shown) or provided from an on-line app store. Moreover, in context, FIG. 1 illustrates at least one embodiment of a journaling system 184 for assisting a user 120 in the use, and or management of a vaporizer device 104, such as for a smoking cessation program.

Figure 2:
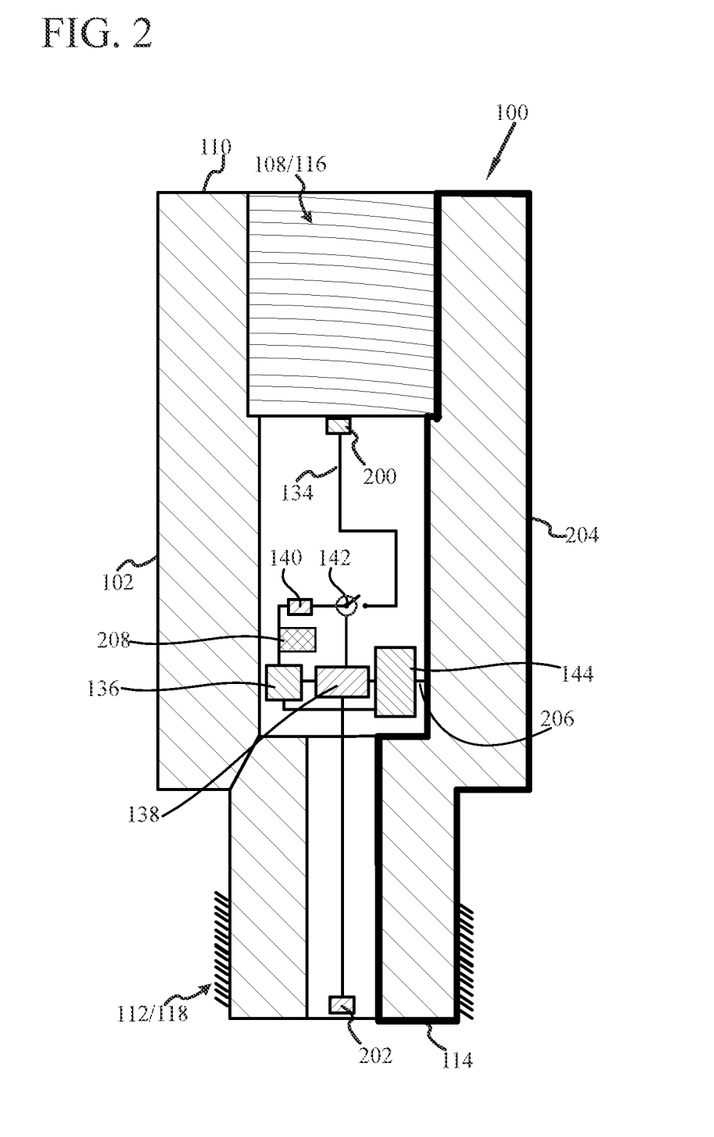
FIG. 2 presents a conceptual cross section plane view of an embodiment for a journaling device in accordance with at least one embodiment of the present invention.

The advantageous nature of the JD 100 to achieve such monitoring and control may be further appreciated with respect to FIG. 2, presenting a conceptual cross sectional side view of JD 100 in accordance with at least one embodiment of the present invention.

As shown in FIG. 2, for at least one embodiment, the JD 100 includes within the housing 102, a first electrical pathway 134, extending from a first terminal 200 to a second terminal 202, at least one controller 138 (such as a processor aka CPU), at least one sensor 140, a wireless transceiver 136, and optionally at least one switch 142 and/or an internal power source 144. These elements may be appreciated to be the control system 130 of the JD 100.

The controller 138, such as a CPU, with associated hardware and memory is adapted to detect a vaporizing event as performed by a connected device or system, such as vaporizer device 104. For at least one embodiment, the controller 138 is a microchip-based controller such as a AVR Attiny Microcontroller provided by Microchip Technology (https://www.microchip.com). Of course, those skilled in the art will appreciate that an alternative Controller may be selected based on specific embodiments desired at the time of manufacturing, as well as parts and inventory commercially available at the time of manufacturer.

The ability to detect a vaporizing event by controller 138 is achieved at least in part with sensor 140. For at least one embodiment, sensor 140 is a current sensor structured and arranged to sense/detect current flow through the first electrical pathway 134. More specifically, for at least one embodiment, the sensor 140, structured and arranged to sense the amperage of the current as provided to the vaporizing system. In varying embodiments, the sensor 140 may also/alternatively sense voltage or other characteristics of the electrical energy as drawn by the vaporizer device 104 from the power supply 106.

It will also be understood and appreciated that the sensor 140 as used and discussed herein, may in actuality be a composite element, comprising a plurality of different sensing components. For at least one embodiment, the sensor 140 is an ACS71240 current sensor IC as provided by Allegro microsystems (https://www.allegromicro.com). Of course, those skilled in the art will appreciate that alternative sensor 140 may be selected based on specific embodiments desired at the time of manufacturing, as well as parts and inventory commercially available at the time of manufacturer.

Moreover, for at least one embodiment of JD 100 intended for use with a vaporizer device 104 that is essentially a simple device activated only for the purpose of vaporizing concentrate, the sensing of any electrical flow to the vaporizer device 104 may be evaluated as a vaporizing event. For at least one alternative embodiment, the flow of electrical current above a pre-determined threshold as reported by the sensor 140 is determined by the controller 138 to be a vaporizing event. The distinction of a threshold event from a non-threshold event may be desired with embodiments of vaporizing systems providing lights or other features that permit a user to see a report of concentrate remaining, electrical assistance for the dispensing of the concentrate, the activation of lights and/or sounds for notification or ambiance, etc.

It will also be appreciated that for at least one embodiment, the controller 138 is further structured and arranged to determine the duration of the vaporization event, such as, but not exclusively limited to determining the duration of the electrical event, or threshold event understood and appreciated to be a vaporizing event. When paired with information regarding coil resistance of the vaporizer within the vaporizer device 104 and quantity dosed, very specific information regarding the dosing event may be determined.

Information regarding the quantity dosed and the configuration of the vaporizing system may be provided by the user through his or her Remote First Computing Device 122, pre-established in the remote dosing system 154, or retrieved by the dosing system 154 in response to a user 120 providing a unique identifier, and/or correlated by one or more identifiers tied to the vaporizer device 104 and/or cartridge with the concentrate to be vaporized, and/or established by the JD 100 itself by communicating with the vaporizer device 104.

The detection of a vaporizing event is communicated by the JD 100 to at least one remote computing device 146 by the controller 138 through the use and activation of the wireless transceiver 136. For at least one embodiment, the wireless transceiver 136 is an NRF52811-CAAA-R IC Bluetooth transceiver from Nordic Semiconductor ASC (https://www.nordicsemi.com), available from DigiKey Electronics (https://www.digikey.com).

For at least one embodiment, the controller 138, sensor 140 and wireless transceiver 136 are powered when and as the vaporizing device 104 completes the circuit as between the positive pole/terminal connection and negative pole/terminal connection points provided by the power supply 106 as extended by the first electrical pathway 134 and the second electrical pathway 204 provided by the JD 100, the second electrical pathway 204 essentially provided by the first coupler 108 the second coupler 112 and the housing itself 102. This second electrical pathway 204 may be considered the ground or negative side of the circuit as provided between the first electrical pathway 134 and second electrical pathway 204. The second electrical pathway 204 is shown as a heavy line on only one side, of the JD 100 but it will be understood and appreciated that for at least one embodiment it is essentially the exterior of the JD 100.

Where the vaporizer device 104 is essentially an on or off device, activated for the purpose of performing a vaporizing event, the flow of current through the JD 100 occurs contemporaneously with the powering of the vaporizing event—and as such the operations of the controller 138, the sensor 140 and the wireless transceiver 136 are essentially in real time and contemporaneous with the powering event.

For at least some embodiments, this limited duration of current flow may be sufficient for the intended purpose of the control system 130 detecting and reporting the occurrence of a vaporizing event by the JD 100. However, for at least some alternative embodiments, additional and advantageous features may be enabled for JD 100, and more specifically the control system 130, by permitting the JD 100 to function independently from the activation of the vaporizer device 104.

For at least one embodiment, this additional period of operation may be achieved by providing at least some embodiments of JD 100 with an internal power source 144, such as a battery or at least a capacitor so that the JD 100 may be at least temporarily powered and operational from time to time regardless of the electrical current flow between the power supply 106 and the vaporizer device 104.

It will be understood and appreciated that for at least one embodiment 144 the internal power source 144 of JD 100 is not sufficient to power the vaporizer device 104. In other words, for at least one embodiment, the JD 100 is not intended to be the power supply for the vaporizer device 104. Moreover, for at least one embodiment, the internal power source 144 is clearly understood and appreciated to be distinct and different from the power supply 106.

For yet another embodiment of JD 100, the control system 130 has an independent electrical connection 206 with the second electrical pathway 204 that permits JD 100, and more specifically at least some of elements of the control system 130, to be powered from the attached power supply 106 regardless of the state of the vaporizer device 104. One or more diodes may be incorporated in the internal electrical pathway 134 and/or the second electrical pathway 204 to prevent an unintended short circuit or parasitic current flow.

For at least some embodiments with the independent electrical connection 206, the JD 100 may still have optional internal power supply 144 such that it may remain at least semi powered when JD 100 is removed from the external power supply 106. In varying embodiments, the internal power source 144 is configured to be charged/recharged by current flow through electrical pathway 144 during activation of the vaporizer device 104, and/or from an external port such as but not limited to a USB port, micro-USB port, USB C port or other USB or the like port. For at least one embodiment, the control system 130 may also include a clock such that the JD 100 may record the time of day of a dosing event.

As a further advantageous element, for at least one embodiment the JD 100 may also include at least one internal switch 142 disposed along the internal electrical pathway 134 such that the JD 100—when installed between the power supply 106 and vaporizer device 104—may prevent use of the vaporizer device 104 based on various factors, such as frequency of use or past duration of a vaporizing event. For embodiments incorporating a more advanced controller 138, and/or the use of the application 124 upon a user Remote First Computing Device 122, the activation or deactivation may be further adjusted by time of day and location, or such other factors as the application 124 may implement—such as an authorization code from the user, bio-data confirmation of the user, etc. . . . . .

Further, for at least one embodiment, the control system 130 may utilize internal switch 142 to influence, if not control the vaporizing process. More specifically, for a given Product, the Dosing System 154 may provide control information regarding the duration of heat application for optimum vaporization of the Product, whether this duration should be continuous, pulsed, or even varied. Such information may be used by the control system 130 and more specifically the controller 138 to control the operation of the vaporizer device. Where switch 142 is a variable device, such as a rheostat or similar device, the controller 138 may be configured to vary the current and further influence the temperature or level of agitation employed to achieve the vaporization event. Further, the controller 138 may cut off power to the vaporizer device 104 to conserve power once the optimum duration of power flow has expired, regardless of whether or not the User 120 continues to maintain the "on switch" or other activator.

In addition to the sensor 140 to detect an electrical event, for at least one embodiment, the JD 100 may further include one or more additional sensor 140 such as an accelerometer 208 or other device structured and arranged to detect an impact event—such as a "click" of a Product dispenser. For at least one embodiment, the accelerometer is a KX222 accelerometer provided by Kionix of Ithaca, New York (https://www.kionix.com).

In other words, some vaporizing systems provide a dispensation system that may include a tactile click event to inform the user of how many units of Product have been dispensed—each click corresponding to a pre-determined amount, i.e. 2 mg or other volume. By noting the number of "clicks" the user may dispense a precise volume of Product. By the JD 100 sensing each dispensation event, the JD 100 may advantageously improve the reporting of the nature of the vaporizing event—e.g., reporting how much concentrate was vaporized in addition to other information as noted above.

Figure 3:
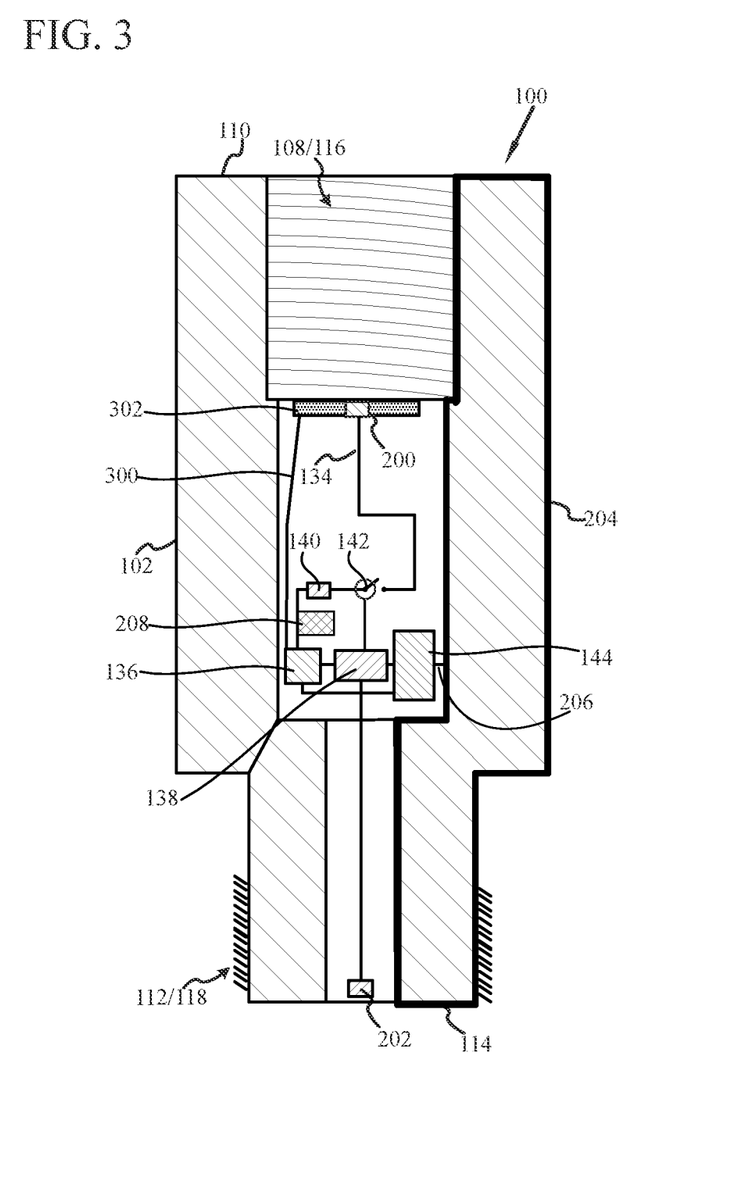
FIG. 3 presents yet another conceptual cross section plane view of an embodiment for a journaling device in accordance with at least one embodiment of the present invention.

FIG. 3 presents an additional embodiment variation for JD 100, further include at least one additional electrical pathway 300 to one or more connectors 302 provided to engage with corresponding connectors of a vaporizer device 104. Such additional connectors may be employed so as to permit the JD 100 to query the vaporizer device 104 for identification information. This information may be encoded to one or more computer chips within the vaporizer device 104, and or one or more computer chips disposed upon or as a component of the cartridge containing the Product that is received by the vaporizer device 104.

Moreover, for at least one embodiment the identification information is provided in a form that may be electronically determined. The identification information may include, and is not limited to, cartridge ID (type of cartridge, specific cartridge ID, optimal settings), batch ID (specific batch identifier that directly links to the producer of the vaporizable substance and its manufacturing information such as use by date, chemical profile/composition, fillers/additives, optimal settings), and vaporizer ID (heater information: coil resistance, thermal properties, manufacturer ID, optimal settings).

In varying embodiments this identification information may be provided directly from the vaporizer device 104 to the JD 100, and more specifically the control system 130 directly by one or more of the electrical pathways (specific data conveying electrical pathways, or as an imposed signal upon the power conducting electrical pathways), or wirelessly by way of the wireless transceiver 136. For yet other embodiments, the identification information may be provided by way of an RFID signal that is received by an embodiment of JD 100 having a control system 130 structured and arranged with an RFID detector.

Moreover, the detection of a vaporizing event and the collection of data associated therewith may vary for different embodiments of JD 100. In light of the above discussion, it will be understood and appreciated that this data regarding the vaporizing event may include, but is not strictly limited to, the duration of the vaporizing event, the time of day of the vaporizing event, the current provided to the vaporizer device 104 during the vaporizing event, the voltage provided to the vaporizer device 104 during the vaporizing event, the number of doses of Product as detected by the JD 100, the location of the vaporizer device 104 during the vaporizing event, and/or such other information as may be desired in varying embodiments for improving the user's experience of the vaporizing event and/or compliance with a program such as a smoking cessation program.

To briefly summarize, for at least one embodiment a JD 100 is provided, including: a housing 102 providing a first coupler 108 at a first end 110 for engaging a hand-held vaporizer device 104 and a second coupler 112 at a second end 114 for engaging a removable power supply 108; the housing 102 substantially enclosing: a first electrical pathway 134 within the housing 102, the first electrical pathway 134 structured and arranged to interconnect the engaged vaporizer device 104 and the removable power supply 108; a switch disposed along the first electrical pathway 134 and operable to interrupt the pathway; at least one sensor 140 structured and arranged to detect at least one event; a processor; a non-volatile memory coupled to the processor having executable instructions to direct the operation of the processor to control the switch and the at least one sensor 140 for the detection of one or more events; a wireless transceiver 136 coupled to the processor and the non-volatile memory and operable to communication with at least one remote computing device 146; and wherein in response to the detection of one or more events by the at least one sensor 140, the processor generating data communicated by the wireless transceiver 136 to the at least one remote computing system.

Embodiments of JD 100 as a distinct element to be disposed between a vaporizer device 104 and power supply 106, provide many advantages. Most notably, as the JD 100 is a distinct component, it may be reused again and again and is not tied to the vaporizer device 104 which may be intended for disposal once the Product has been depleted, and it likewise is not tied to the power supply 106 which may not be rechargeable and therefore intended for disposal once drained. Even where the vaporizer device 104 is refillable and the power supply 106 rechargeable, some Users 120 may prefer the JD 100 as a separate device as mechanical wear and tear and/or new design options may make new vaporizing devices 104 more desirable, and even with ever improving technologies, rechargeable batteries often degrade over time. The stand-alone embodiment of JD 100 also permits a User 120 to incorporate the use of the JD 100 with his or her existing vaporizer device 104 and power supply which may be comforting when he or she is embarking on a Product cessation program.

Figure 4:
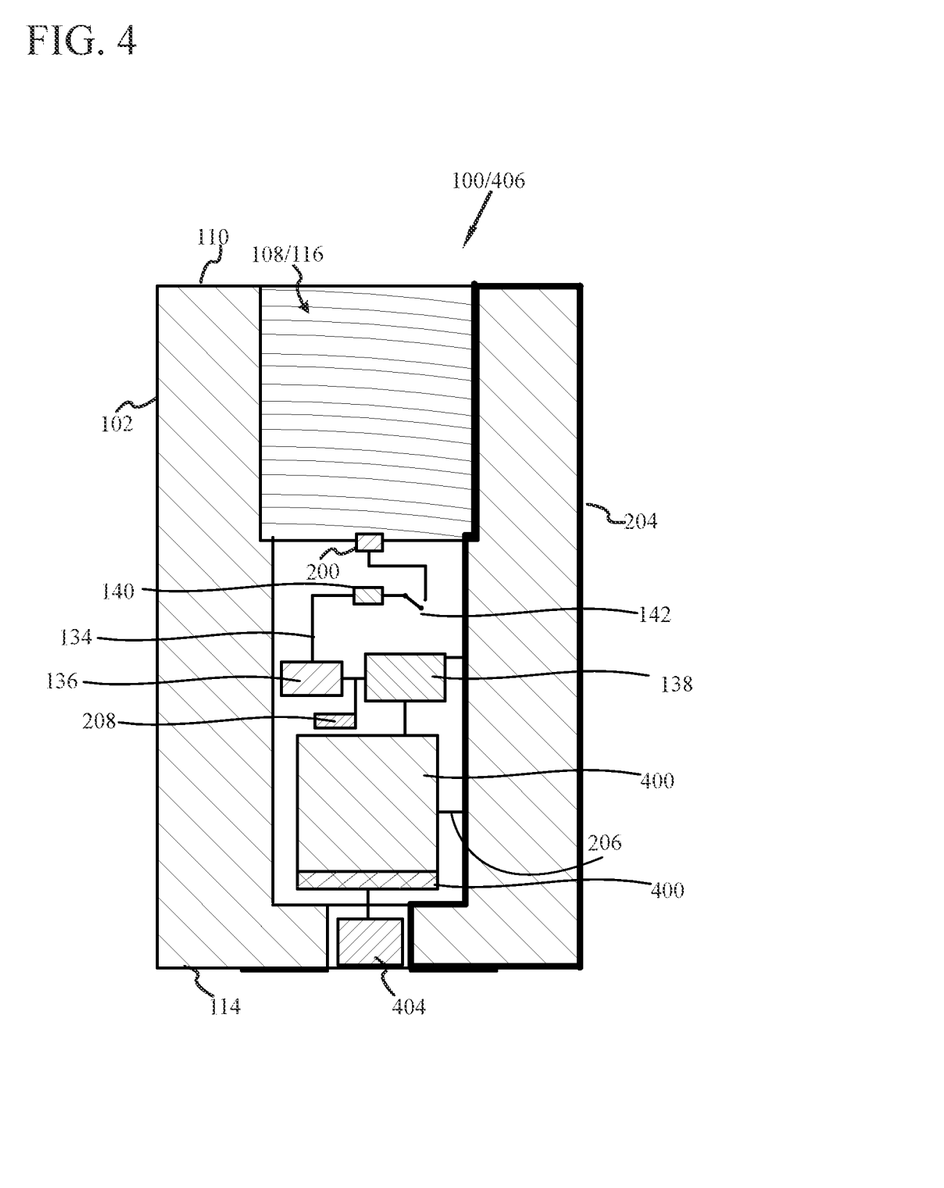
FIG. 4 presents yet another conceptual cross section plane view of an embodiment for a journaling device as a journaling battery in accordance with at least one embodiment of the present invention.

Still, it will be understood and appreciated that for at least one alternative embodiment, the JD 100 may further incorporate a sufficient power supply so as to replace the intended power supply 106. Moreover, as shown in FIG. 4, an alternative embodiment of a JD 100 incorporates a power supply 400 of sufficient size and capacity to power the vaporizer device 104.

Such a configuration may further include a charging port 402, or internal circuitry 404 to permit inductive charging, so as to recharge the internal battery when and as desired. The embodiment of JD 100 having an internal power supply 400 as shown will be appreciated to have substantially the same control system 130 as described above with respect to FIGS. 2 & 3. In addition, at least one embodiment of enhanced JD 100 may also provide additional information output devices, such as a display or indicator lights that may provide useful information to the User 120 such as, but not limited to the status of the remaining battery charge, the last dosage of Product, the time of the last vaporizing event, and/or such other information as may be deemed appropriate in varying embodiments.

Moreover, for at least one embodiment the JD 100 may be viewed or considered as a journaling battery 406 by the user or other involved parties, the journaling battery 406 incorporating at least the base elements of the JD 100 as noted and discussed above—specifically the control system 130, e.g., a controller 138, wireless transceiver 136, sensor 140, and optionally a switch 142 or other components.

Various methods of providing a JD 100, aka journaling adapter, may be understood and appreciated to provide a device in accordance with one or more of the structural embodiments as described above. These methods may be further augmented by incorporating use of the journaling device, aka journaling adapter to monitor and report to at least one remote computing system each detected vaporizing event as performed by an attached vaporizing device or system.

Indeed, for at least one embodiment, a. method for using a JD 100 may be summarized as, providing a JD 100 comprising: a housing 102 providing a first coupler 108 at a first end 110 for engaging a hand-held vaporizer device 104 and a second coupler 112 at a second end 114 for engaging a removable power supply 108; the housing 102 substantially enclosing: a first electrical pathway 134 within the housing 102, the first electrical pathway 134 structured and arranged to interconnect the engaged vaporizer device 104 and the removable power supply 106; a switch disposed along the first electrical pathway 134 and operable to interrupt the pathway; at least one sensor 140 structured and arranged to detect at least one event; a processor; a non-volatile memory coupled to the processor having executable instructions to direct the operation of the processor to control the switch and the at least one sensor 140 for the detection of one or more events; a wireless transceiver 136 coupled to the processor and the non-volatile memory and operable to communication with at least one remote computing device 146; and wherein in response to the detection of one or more events by the at least one sensor 140, the processor generating data communicated by the wireless transceiver 136 to the at least one remote computing system; disposing the JD 100 between a vaporizer device 104 and a removable power supply 106; sensing a flow of current through the first electrical pathway 134 to detect a vaporizing event; and reporting at least the vaporizing event to the at least one remote computing device 146.

With respect to the above descriptions of varying embodiments of JD 100 as provided in FIGS. 2 and 3, and with respect to the greater system view presented in FIG. 1, it may be further understood and appreciated that for at least one embodiment the detection of a vaporization event by JD 100 is reported by the control system 130 of JD 100 to the Remote First Computing Device 122 and App 124 which are embodiments or adaptations of the systems and methods set forth in the '829 app and/or '556 app as noted above and incorporated by reference.

More specifically, whether recorded locally by the JD 100 or remotely by a user's computing device in communication with the JD 100, the user's vaporization event may be used to establish a usage history which may be of value and assistance regarding confirming the user's proper usage of the vaporizing system for medical, recreational or cessation purposes. It is of course understood and appreciated that as the JD 100 is intended for easy and user performed installation between the vaporization system and the power supply, e.g., the 510-battery, the JD 100 can of course be removed and thereby disabled. However, such an action may be noted by a third party overseeing the user who may then withhold a further prescription of Product, seek to counsel the user in the benefits of using the JD 100 for their intended treatment, or otherwise take positive intervention. Even when used on a solo user basis, the knowledge that the JD 100 can be removed may be insignificant and not acted upon as the assistance provided to the user by the JD 100 in keeping with his or her intended use regiment may be of greater interest and/or value.

Figure 5:
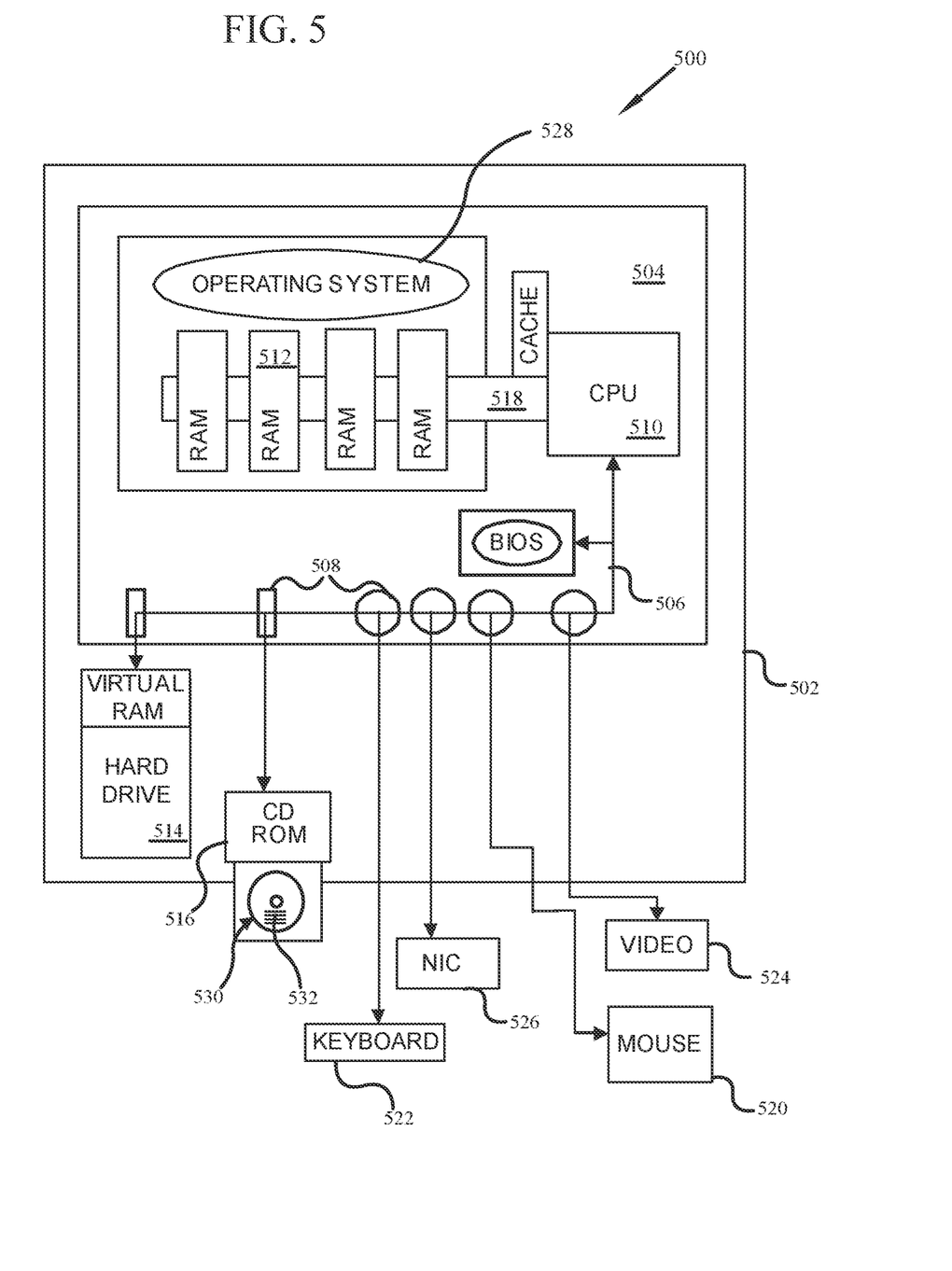
FIG. 5 high-level block diagram of a computer system in accordance with at least one embodiment.

To expand upon the initial suggestion of at least the JD 100, Remote First Computing Device 122, remote computing device 146, Dosing System 154, and other systems described herein being computer systems adapted to their specific roles, FIG. 5 is a high level block diagram of an exemplary computer system 500 such as may be provided for one or more of the elements comprising at least the JD 100, Remote First Computing Device 122, remote computing device 146, or Dosing System 154, whether provided as distinct individual systems or integrated together in one or more computer systems.

Computer system 500 has a case 502, enclosing a main board 504. The main board 504 has a system bus 506, connection ports 508, a processing unit, such as Central Processing Unit (CPU) 510 with at least one microprocessor (not shown) and a memory storage device, such as main memory 512, hard drive 514 and CD/DVD ROM drive 516.

Memory bus 518 couples main memory 512 to the CPU 510. A system bus 506 couples the hard disc drive 514, CD/DVD ROM drive 516 and connection ports 508 to the CPU 510. Multiple input devices may be provided, such as, for example, a mouse 520 and keyboard 522. Multiple output devices may also be provided, such as, for example, a video monitor 524 and a printer (not shown). As computer system 500 is intended to be interconnected with other computer systems in the journaling system 184 a combined input/output device such as at least one network interface card, or NIC 526 is also provided.

Computer system 500 may be a commercially available system, such as a desktop workstation unit provided by IBM, Dell Computers, Gateway, Apple, or other computer system provider, or portable hand-held computing devices such as an iPhone®, Android® or another portable computing device. Computer system 500 may also be a networked computer system, wherein memory storage components such as hard drive 514, additional CPUs 510 and output devices such as printers are provided by physically separate computer systems commonly connected together in the network.

Those skilled in the art will understand and appreciate that the physical composition of components and component interconnections are comprised by the computer system 500, and select a computer system 500 suitable for one or more of the computer systems incorporated in the formation and operation of JD 100 or other computing systems as described herein.

When computer system 500 is activated, preferably an operating system 528 will load into main memory 512 as part of the boot strap startup sequence and ready the computer system 500 for operation. At the simplest level, and in the most general sense, the tasks of an operating system fall into specific categories, such as, process management, device management (including application and User interface management) and memory management, for example. The form of the computer-readable medium 530 and language of the program 532 are understood to be appropriate for and functionally cooperate with the computer system 500.

Moreover, variations of computer system 500 may be adapted to provide the physical elements of one or more components comprising each at least JD 100, Remote First Computing Device 122, remote computing device 146, Dosing System 154, and the switches, routers and such other components as may be desired and appropriate for the methods and systems a dosing vaporizer journaling adapter, aka journaling device.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A vaporizer journaling device as a distinct component for external attachment between a vaporizer and a power supply, the vaporizer journaling device comprising:
    a housing providing a first coupler at a first end for engaging a hand-held vaporizer device and a second coupler at a second end for engaging a removable power supply; the housing substantially enclosing:
        a first electrical pathway within the housing, the first electrical pathway structured and arranged to interconnect the engaged vaporizer device and the removable power supply;
        a wireless transceiver structured and arranged for wireless communication with at least one remote computing device;
        a control system having at least one processor, the control system structured and arranged to:
            sense a flow of current through the first electrical pathway to the vaporizer device;
            detect a vaporizing event; and
            communicate by the wireless transceiver each vaporizing event to the at least one remote computing device.

2. The vaporizer journaling device of claim 1, wherein the removable power supply is a 510-battery.

3. The vaporizer journaling device of claim 1, wherein the first coupler is a female threaded 510-terminal coupler, and the second coupler is a male threaded 510-terminal coupler.

4. The vaporizer journaling device of claim 1, wherein the first coupler, the second coupler and the housing provide a second electrical pathway structured and arranged to interconnect the engaged vaporizer device and the removable power supply.

5. The vaporizer journaling device of claim 1, wherein the control system is further structured and arranged to receive identification information from an engaged hand-held vaporizer device or the remote computing device.

6. The vaporizer journaling device of claim 5, wherein the identification information identifies a product contained by the hand-held vaporizer device for vaporization.

7. The vaporizer journaling device of claim 5, wherein the identification information uniquely identifies the vaporizer device.

8. The vaporizer journaling device of claim 5, wherein the identification information uniquely identifies a cartridge of concentrate disposed within the vaporizer device.

9. The vaporize journaling device of claim 5, wherein the identification information uniquely identifies the concentrate to be vaporized by the vaporizer device.

10. The vaporizer journaling device of claim 1, wherein the communication of each vaporizing event includes data selected from the group consisting of: duration of the vaporizing event, current provided to the vaporizing device the vaporizing event, voltage provided to the vaporizing device during the vaporizing event, and/or number of doses of a Product vaporized during the vaporizing event.

11. The vaporizer journaling device of claim 1, further including an internal power supply.

12. The vaporizer journaling device of claim 1, further including at least one electrical switch disposed upon the first electrical pathway, the control system further operable to control the switch to interrupt the first electrical pathway.

13. The vaporizer journaling device of claim 1, wherein the control system comprises:
    a switch disposed along the first electrical pathway and operable to interrupt the pathway;
    at least one sensor structured and arranged to detect at least one event;
    a processor;
    a non-volatile memory coupled to the processor having executable instructions to direct the operation of the processor to control the switch and the at least one sensor for the detection of one or more events.

14. The vaporizer journaling device of claim 1, further comprising:
    a remote server system having a processor and a database of products vaporizable by the vaporizing device;
    at least one remote application for installation upon a remote computing device having a processor and a second wireless transceiver controlled by the processor, the second wireless transceiver structured and arranged for wireless communication with the vaporizer journaling device and the remote server system;
    wherein in response to a user indicating a desire for a vaporization event to the remote application, the remote computing device communicating with the database of the remote server to confirm the user as authorized for the vaporization event, and in response to authorization, communicating with the journaling device to permit interconnection of the removable power supply to the vaporizer device to permit vaporization.

15. The vaporizer journaling device of claim 1, wherein the journaling device is reusable.

16. A vaporizer journaling device as a stand-alone component for external attachment between a vaporizer and a power supply, the vaporizer journaling device comprising:
    a housing providing a first coupler at a first end for engaging a hand-held vaporizer device and a second coupler at a second end for engaging a removable power supply; the housing substantially enclosing;
        a first electrical pathway within the housing, the first electrical pathway structured and arranged to interconnect the engaged vaporizer device and the removable power supply;
        a switch disposed along the first electrical pathway and operable to interrupt the pathway;
        at least one sensor structured and arranged to detect at least one event;
        a processor;
        a non-volatile memory coupled to the processor having executable instructions to direct the operation of the processor to control the switch and the at least one sensor for the detection of one or more events;
a wireless transceiver coupled to the processor and the non-volatile memory and operable to communication with at least one remote computing device; and
wherein in response to the detection of one or more events by the at least one sensor, the processor generating data communicated by the wireless transceiver to the at least one remote computing system.

17. The vaporizer journaling device of claim 16, wherein the removable power supply is a 510-battery.

18. The vaporizer journaling device of claim 16, wherein the first coupler is a female threaded 510-terminal coupler, and the second coupler is a male threaded 510-terminal coupler.

19. The vaporizer journaling device of claim 16, wherein the first coupler, the second coupler and the housing provide a second electrical pathway structured and arranged to interconnect the engaged vaporizer device and the removable power supply.

20. The vaporizer journaling device of claim 16, wherein the at least one sensor is selected from the group consisting of: a current sensor, an accelerometer, a voltage sensor.

21. The vaporizer journaling device of claim 16, wherein the at least one event is an electrical current flow along the first electrical pathway of at least a predetermined threshold.

22. The vaporizer journaling device of claim 16, wherein the control system is further structured and arranged to receive identification information from an engaged hand-held vaporizer device or the remote computing device.

23. The vaporizer journaling device of claim 22, wherein the identification information identifies a product contained by the hand-held vaporizer device for vaporization.

24. The vaporizer journaling device of claim 22, wherein the identification information uniquely identifies the vaporizer device.

25. The vaporizer journaling device of claim 22, wherein the identification information uniquely identifies a cartridge of concentrate disposed within the vaporizer device.

26. The vaporizer journaling device of claim 22, wherein the identification information uniquely identifies the concentrate to be vaporized by the vaporizer device.

27. The vaporizer journaling device of claim 16, wherein the communication of each vaporizing event includes data selected from the group consisting of: duration of the vaporizing event, current provided to the vaporizing device the vaporizing event, voltage provided to the vaporizing device during the vaporizing event, and/or number of doses of a Product vaporized during the vaporizing event.

28. The vaporizer journaling device of claim 16, further including an internal power supply.

29. The vaporizer journaling device of claim 16, further comprising:
a remote server system having a processor and a database of products vaporizable by the vaporizing device;
at least one remote application for installation upon a remote computing device having a processor and a second wireless transceiver controlled by the processor, the second wireless transceiver structured and arranged for wireless communication with the vaporizer journaling device and the remote server system;
wherein in response to a user indicating a desire for a vaporization event to the remote application, the remote computing device communicating with the database of the remote server to confirm the user as authorized for the vaporization event, and in response to authorization, communicating with the journaling device to permit interconnection of the removable power supply to the vaporizer device to permit vaporization.

30. The vaporizer journaling device of claim 16, wherein the journaling device is reusable.

31. A method for using a vaporizer device as a distinct component for external attachment between a vaporizer and a power supply, the vaporizer journaling device comprising, comprising:
providing a journaling device comprising:
a housing providing a first coupler at a first end for engaging a hand-held vaporizer device and a second coupler at a second end for engaging a removable power supply; the housing substantially enclosing:
a first electrical pathway within the housing, the first electrical pathway structured and arranged to interconnect the engaged vaporizer device and the removable power supply;
a switch disposed along the first electrical pathway and operable to interrupt the pathway;
at least one sensor structured and arranged to detect at least one event;
a processor;
a non-volatile memory coupled to the processor having executable instructions to direct the operation of the processor to control the switch and the at least one sensor for the detection of one or more events;
a wireless transceiver coupled to the processor and the non-volatile memory and operable to communication with at least one remote computing device; and
wherein in response to the detection of the one or more events by the at least one sensor, the processor generating data communicated by the wireless transceiver to the at least one remote computing system;
disposing the journaling device between a vaporizer device and a removable power supply;
sensing a flow of current through the first electrical pathway to detect a vaporizing event; and
reporting at least the vaporizing event to the at least one remote computing device.

32. The method for using a vaporizer journaling device of claim 31, further comprising:
a remote server system having a processor and a database of products vaporizable by the vaporizing device;
at least one remote application for installation upon a remote computing device having a processor and a second wireless transceiver controlled by the processor, the second wireless transceiver structured and arranged for wireless communication with the vaporizer journaling device and the remote server system;
wherein in response to a user indicating a desire for a vaporization event to the remote application, the remote computing device communicating with the database of the remote server to confirm the user as authorized for the vaporization event, and in response to authorization, communicating with the journaling device to permit interconnection of the removable power supply to the vaporizer device to permit vaporization.

33. The method of claim 31, wherein the journaling device is reusable.

* * * * *